US010861250B2

(12) United States Patent
Long et al.

(10) Patent No.: US 10,861,250 B2
(45) Date of Patent: Dec. 8, 2020

(54) TECHNOLOGIES FOR MERGING THREE-DIMENSIONAL MODELS OF DENTAL IMPRESSIONS

(71) Applicant: SDC U.S. SmilePay SPV, Nashville, TN (US)

(72) Inventors: Josh Long, Nashville, TN (US); Andrew Wright, Nashville, TN (US); Christopher Yancey, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 16/548,712

(22) Filed: Aug. 22, 2019

(65) Prior Publication Data

US 2019/0378344 A1    Dec. 12, 2019

Related U.S. Application Data

(63) Continuation-in-part of application No. 16/257,692, filed on Jan. 25, 2019, now Pat. No. 10,410,435, which is a continuation-in-part of application No. 16/165,439, filed on Oct. 19, 2018, which is a continuation of application No. 15/825,760, filed on Nov. 29, 2017, now Pat. No. 10,109,114.

(51) Int. Cl.
*G06T 19/20* (2011.01)

(52) U.S. Cl.
CPC ......... *G06T 19/20* (2013.01); *G06T 2210/41* (2013.01); *G06T 2219/2004* (2013.01)

(58) Field of Classification Search
CPC ............... G06T 19/20; G06T 2210/41; G06T 2219/2004
See application file for complete search history.

(56) References Cited

U.S. PATENT DOCUMENTS

| | | | | |
|---|---|---|---|---|
| 5,886,702 A | * | 3/1999 | Migdal | ................... G06T 17/20 345/423 |
| 5,945,996 A | * | 8/1999 | Migdal | ................... G06T 17/20 345/420 |
| 6,208,347 B1 | * | 3/2001 | Migdal | ................... G06T 17/20 345/419 |
| 7,698,014 B2 | * | 4/2010 | Dunne | ................. A61B 5/4547 700/118 |
| 7,702,492 B2 | | 4/2010 | Marshall | |

(Continued)

OTHER PUBLICATIONS

International Search Report and Written Opinion for International Application No. PCT/US2018/062824, dated Jan. 2, 2019, 8 pages.

*Primary Examiner* — Abderrahim Merouan
(74) *Attorney, Agent, or Firm* — Foley & Lardner LLP

(57) ABSTRACT

A computing device for dental impression scan merging includes a processor configured to generate a first model and a second model including a first and second plurality of geometric faces indicative of a first and second dental arch of a user. The processor generates a first point cloud of the first model and a second point cloud of the second model. The processor aligns the first point cloud and the second point cloud. The processor merges the first and second model to generate a merged model where merging the first and second model is based on the alignment of the first point cloud and the second point cloud.

20 Claims, 11 Drawing Sheets

(56) References Cited

U.S. PATENT DOCUMENTS

| | | |
|---|---|---|
| 7,831,322 B2 | 11/2010 | Liu et al. |
| 8,234,000 B2 * | 7/2012 | Andersson ............ A61C 9/0006 |
| | | 700/98 |
| 8,995,732 B2 * | 3/2015 | Kaza .................... A61C 9/0046 |
| | | 382/128 |
| 9,301,814 B2 | 4/2016 | Kaza et al. |
| 9,626,462 B2 * | 4/2017 | Somasundaram ... A61B 5/4547 |
| 9,684,952 B2 * | 6/2017 | Carlson ................. A61B 6/032 |
| 9,829,710 B1 | 11/2017 | Newell et al. |
| 9,839,494 B2 | 12/2017 | Kaza et al. |
| 10,143,537 B2 | 12/2018 | Kaza et al. |
| 10,162,908 B1 * | 12/2018 | Bhaskara ................ G06F 30/00 |
| 10,335,252 B2 | 7/2019 | Kaza et al. |
| 10,398,539 B2 * | 9/2019 | Nilsson ............... A61C 13/0004 |
| 10,405,947 B1 | 9/2019 | Kaza et al. |
| 2006/0040236 A1 | 2/2006 | Schmitt |
| 2006/0204078 A1 | 9/2006 | Orth et al. |
| 2006/0263738 A1 * | 11/2006 | Kuo ......................... A61C 7/00 |
| | | 433/24 |
| 2006/0275736 A1 * | 12/2006 | Wen ......................... A61C 9/00 |
| | | 433/213 |
| 2007/0207437 A1 | 9/2007 | Sachdeva et al. |
| 2008/0206705 A1 * | 8/2008 | Kaza ....................... G16B 5/00 |
| | | 433/71 |
| 2009/0148816 A1 | 6/2009 | Marshall et al. |
| 2009/0160855 A1 | 6/2009 | Wu |
| 2009/0220134 A1 | 9/2009 | Cahill et al. |
| 2009/0316966 A1 * | 12/2009 | Marshall ............... A61B 6/5217 |
| | | 382/128 |
| 2010/0324875 A1 | 12/2010 | Kalili |
| 2011/0196653 A1 | 8/2011 | Lajoie et al. |
| 2011/0200248 A1 * | 8/2011 | Matabosch I Gerones ................ |
| | | G06K 9/00214 |
| | | 382/154 |
| 2012/0015316 A1 | 1/2012 | Sachdeva et al. |
| 2012/0330447 A1 * | 12/2012 | Gerlach ................. G01B 11/24 |
| | | 700/95 |
| 2014/0026419 A1 | 1/2014 | Haber |
| 2014/0037194 A1 * | 2/2014 | Kitamura ............... G01B 11/24 |
| | | 382/154 |
| 2014/0051037 A1 * | 2/2014 | Fisker .................... A61C 8/0048 |
| | | 433/213 |
| 2014/0203463 A1 | 7/2014 | Haber |
| 2014/0254919 A1 | 9/2014 | Sun et al. |
| 2015/0182316 A1 | 7/2015 | Morales et al. |
| 2015/0199839 A1 * | 7/2015 | Chon .................... G06T 3/0037 |
| | | 345/427 |
| 2015/0264299 A1 | 9/2015 | Leech et al. |
| 2015/0348320 A1 | 12/2015 | Pesach et al. |
| 2016/0148375 A1 * | 5/2016 | Oh ......................... G06T 11/008 |
| | | 382/131 |
| 2016/0220200 A1 | 8/2016 | Sandholm et al. |
| 2016/0324597 A1 | 11/2016 | Colby |
| 2017/0061588 A1 * | 3/2017 | Lee ......................... G06T 7/248 |
| 2017/0312060 A1 | 11/2017 | Morales et al. |
| 2017/0340390 A1 * | 11/2017 | Harbison ................ A61B 34/10 |
| 2017/0345147 A1 | 11/2017 | Ohtake et al. |
| 2018/0025496 A1 * | 1/2018 | Lindner .................... G06T 7/50 |
| | | 382/154 |
| 2018/0091169 A1 | 3/2018 | Colby |
| 2018/0350134 A1 * | 12/2018 | Lodato .................... G06T 17/20 |
| 2019/0246000 A1 | 8/2019 | Cheng et al. |
| 2019/0282344 A1 | 9/2019 | Azernikov et al. |
| 2019/0388188 A1 | 12/2019 | Kaza et al. |

* cited by examiner

TECHNOLOGIES FOR MERGING THREE-DIMENSIONAL MODELS OF DENTAL IMPRESSIONS

CROSS REFERENCE TO RELATED PATENT APPLICATIONS

This application is a continuation-in-part of U.S. patent application Ser. No. 16/257,692 filed Jan. 25, 2019, which is continuation-in-part of U.S. patent application Ser. No. 16/165,439 filed Oct. 19, 2018, which is a continuation of U.S. patent application Ser. No. 15/825,760 filed Nov. 29, 2017, now U.S. Pat. No. 10,109,114, each of which are hereby incorporated by reference in their entirety.

TECHNICAL FIELD

The present disclosure relates to three-dimensional computer modeling and, more specifically, to a system and method for merging three-dimensional models of dental impressions.

BACKGROUND

A dental impression provides a negative imprint of the teeth and tissues in the mouth. The negative impression may then be utilized to produce a physical or digital reproduction of the teeth, e.g., dentures and orthodontics. Generally, a dental tray having a viscous, thixotropic impression material therein is fit over the dental arches of the patient. The impression material sets to a solid, leaving an imprint of the structures in the mouth. When removed from the mouth, the impression provides a detailed and stable negative of the teeth. Optionally, the impression is processed using digital scanning methods to create the digital negative of the teeth.

Traditionally, dental impressions are made in a dental office and require significant time. The impressions are then delivered to an outside vendor that utilizes the impression to form a positive model of the teeth. If the dental impression includes any errors, e.g., an incomplete impression of the teeth and tissues, the patient may be required to return to the dental office to have a second impression made.

As an alternative method to traditional orthodontic procedures, in less severe cases, dental impressions may be made with an at-home dental impression kit. Such kits are generally prescribed by a dental professional to qualified customers, e.g., in a dental office. The user may then administer the contents of the dental impression kit at home. After completing the dental impressions, the kit is returned to the dental professional. Some at-home kits may be difficult to administer and/or may result in poor quality dental impressions.

SUMMARY

One embodiment relates to a computing device for dental impression scan merging. The computing device includes a processor configured to generate a first model and a second model. The first model includes a first three-dimensional model including a first plurality of geometric faces indicative of a first dental impression of a dental arch of a user, and the second model includes a second three-dimensional model including a second plurality of geometric faces indicative of a second dental impression of the same dental arch of the user. The processor is configured to generate a first point cloud of the first model and a second point cloud of the second model. The processor is configured to align the first point cloud and the second point cloud. The processor is configured to merge the first model and the second model to generate a merged model. Merging the first model and the second model is based on the alignment of the first point cloud and the second point cloud.

Another embodiment relates to a method for dental impression scan merging. The method includes generating, by a computing device, a first model and a second model. The first model includes a three-dimensional model including a plurality of geometric faces indicative of a first dental impression of a user's dental arch. The second model includes a three dimensional model including a plurality of geometric faces indicative of a second dental impression of the user's dental arch. The first dental impression and the second dental impression are impressions of the same dental arch of the user. The method includes generating a first point cloud of the first model and a second point cloud of the second mode. The method includes aligning the first point cloud and the second point cloud. The method includes merging the first model and the second model to generate a merged model. Merging the first model and the second model is based on the alignment of the first point cloud and the second point cloud.

Another embodiment relates to a computing device for dental impression scan merging. The computing device includes a processing circuit including a processor and memory. The memory stores instructions that, when executed by the processor, cause the processor to generate a first model and a second model. The first model includes a three-dimensional model including a plurality of geometric faces indicative of a first dental impression of a user's dental arch. The second model includes a three dimensional model including a plurality of geometric faces indicative of a second dental impression of the user's dental arch. The first dental impression and the second dental impression are impressions of the same dental arch of the user. The memory further stores instructions to generate a first point cloud for the first model and a second point cloud for the second model. Generating the first point cloud and the second point cloud includes, for each of the first model and the second model, identifying vertices of the plurality of geometric faces, and generating, using the vertices of the plurality of geometric faces, points that together define a point cloud for the respective model. The memory further stores instructions to compute, using the first point cloud and the second point cloud, a translation matrix. The memory further stores instructions to shift the first point cloud with respect to the second point cloud based on the translation matrix to align the first point cloud and the second point cloud. The memory further stores instructions to generate a merged model that includes data from the first model and the second model based on the alignment of the first point cloud and the second point cloud.

BRIEF DESCRIPTION OF THE DRAWINGS

The foregoing and other features of the various embodiments of the methods and apparatuses described herein will become more apparent from the following detailed description and the accompanying drawings in which.

DETAILED DESCRIPTION

Figure 1:
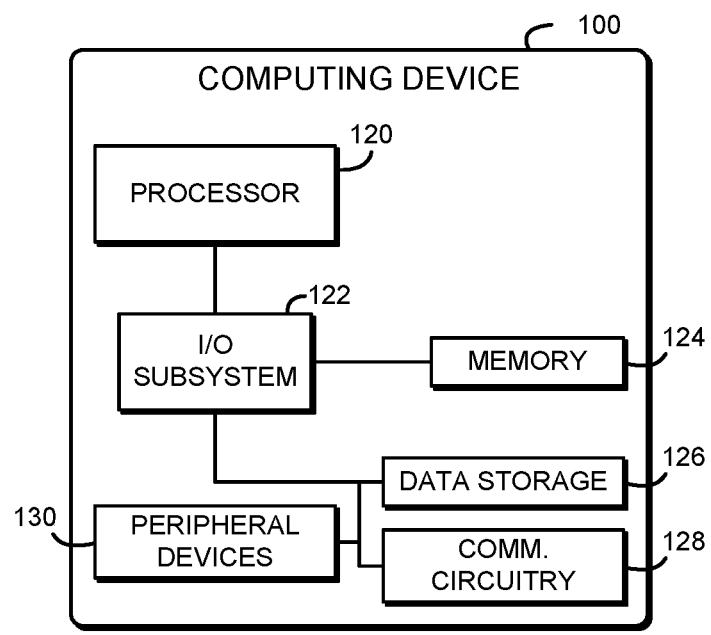
FIG. 1 is a block diagram of at least one embodiment of a computing device for merging three-dimensional models.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure as defined by the appended claims.

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

Referring now to FIG. 1, an illustrative computing device 100 for merging three-dimensional models of dental impressions is shown. In use, as described further below, the computing device 100 generates or otherwise acquires three-dimensional models for each of multiple dental impressions. For example, multiple dental impressions created by a user with an at-home dental impression kit may be scanned to generate the three-dimensional models. The computing device 100 automatically merges geometry from the models to generate a complete model of one or more of the user's dental arches. In some embodiments, the computing device 100 may use multiple merge strategies and select the best merged model. Thus, the computing device 100 may generate a higher-quality merged model as compared to any of the individual models. Additionally, the computing device 100 may be able to generate a complete model from multiple incomplete dental impressions, which may improve the proportion of at-home dental kits that are successfully completed and/or reduce the number of retake impression kits that are sent to users (e.g., customers).

The computing device 100 may be embodied as any type of computation or computer device capable of performing the functions described herein, including, without limitation, a computer, a server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. As such, the computing device 100 may be embodied as a single server computing device or a collection of servers and associated devices. For example, in some embodiments, the computing device 100 may be embodied as a "virtual server" formed from multiple computing devices distributed across a network and operating in a public or private cloud. Accordingly, although the computing device 100 is illustrated in FIG. 1 and described below as embodied as a single server computing device, it should be appreciated that the computing device 100 may be embodied as multiple devices cooperating together to facilitate the functionality described below.

As shown in FIG. 1, the computing device 100 illustratively include a processor 120, an input/output subsystem 122, a memory 124, a data storage device 126, and a communication subsystem 128, and/or other components and devices commonly found in a server computer or similar computing device. Of course, in other embodiments, the computing device 100 may include other or additional components, such as those commonly found in a server computer (e.g., various input/output devices). Additionally, in some embodiments, one or more of the illustrative components may be incorporated in, or otherwise form a portion of, another component. For example, the memory 124, or portions thereof, may be incorporated in the processor 120.

The processor 120 may be embodied as any type of processor capable of performing the functions described herein. The processor 120 may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the computing device 100, such as operating systems, applications, programs, libraries, and drivers. The memory 124 is communicatively coupled to the processor 120 via the I/O subsystem 122, which may be embodied as circuitry and/or components to facilitate input/output operations with the processor 120, the memory 124, and other components of the computing device 100. For example, the I/O subsystem 122 may be embodied as, or otherwise include, memory controller hubs, input/output control hubs, platform controller hubs, integrated control circuitry, firmware devices, communication links (i.e., point-to-point links, bus links, wires, cables, light guides, printed circuit board traces, etc.) and/or other components and subsystems to facilitate the input/output operations. In some embodiments, the I/O subsystem 122 may form a portion of a system-on-a-chip (SoC) and be incorporated, along with the processor 120, the memory 124, and other components of the computing device 100, on a single integrated circuit chip.

The data storage device 126 may be embodied as any type of device or devices configured for short-term or long-term storage of data such as, for example, memory devices and circuits, memory cards, hard disk drives, solid-state drives, or other data storage devices. The communication subsystem 128 of the computing device 100 may be embodied as any communication circuit, device, or collection thereof, capable of enabling communications between the computing device 100 and other remote devices over a network. The communication subsystem 128 may be configured to use any one or more communication technology (e.g., wired or wireless communications) and associated protocols (e.g., Ethernet, InfiniBand®, Bluetooth®, WiMAX, etc.) to effect such communication.

As shown, the computing device 100 may also include one or more peripheral devices 130. The peripheral devices 130 may include any number of additional input/output devices, interface devices, and/or other peripheral devices. For example, in some embodiments, the peripheral devices 130 may include a display, touch screen, graphics circuitry, keyboard, mouse, speaker system, microphone, network interface, and/or other input/output devices, interface devices, and/or peripheral devices.

Figure 2:
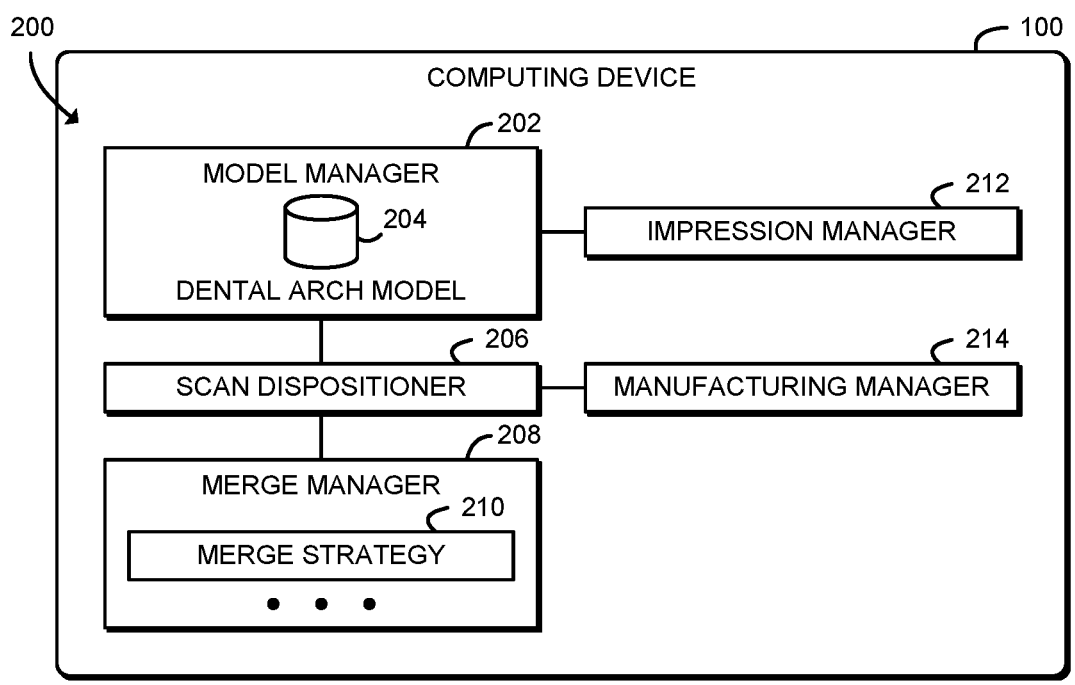
FIG. 2 is a block diagram of at least one embodiment of an environment that may be established by the computing device of FIG. 1.

Referring now to FIG. 2, in an illustrative embodiment, the computing device 100 establishes an environment 200 during operation. The illustrative environment 200 includes model manager 202, a scan dispositioner circuitry 206, a merge manager 208, an impression manager 212, and a manufacturing manager 214. The various components of the environment 200 may be embodied as hardware, firmware, software, or a combination thereof. As such, in some embodiments, one or more of the components of the environment 200 may be embodied as circuitry or collection of electrical devices (e.g., model manager circuitry 202, scan dispositioner circuitry 206, merge manager circuitry 208, impression manager circuitry 212, and/or manufacturing manager circuitry 214). It should be appreciated that, in such embodiments, one or more of the model manager circuitry 202, the scan dispositioner circuitry 206, the merge manager circuitry 208, the impression manager circuitry 212, and/or the manufacturing manager circuitry 214 may form a portion of one or more of the processor 120, the I/O subsystem 122, and/or other components of the computing device 100. For instance, the model manager 202, merge manager 208, manufacturing manager 214, etc. may be implemented as one or more processor(s) 120 of the computing device 100, as one or more processing circuits, or other types of hardware. Additionally, in some embodiments, one or more of the illustrative components may form a portion of another component and/or one or more of the illustrative components may be independent of one another.

The model manager 202 is configured to generate multiple models 204. Each model 204 may be embodied as a three-dimensional model indicative of a dental impression of a client's dental arch (e.g., mandibular arch or maxillary arch). The models 204 may be generated by scanning the corresponding dental impression to generate the model 204. Although illustrated as a model of dental impressions, in some embodiments, each model 204 may be embodied as a three-dimensional model of a different physical object. As described below, the model manager 202 may be further configured to generate additional models 204 if a merged model 204 is not indicative of the complete anatomy of a customer's dental arch.

The scan dispositioner circuitry 206 is configured to determine whether a model 204 (including a merged model 204) is indicative of a complete anatomy of the customer's dental arch. That determination may be based on quality review data provided for each model 204 by a technician.

The merge manager 208 is configured to merge two models 204 using a merge strategy 210 to generate a merged model 204 if an original input model 204 is not indicative of the complete anatomy of the customer's dental arch. Each merge strategy 210 may be embodied as any algorithm, process, policy, or other strategy that may be used to select geometry from the input models 204 to be included in the merged model 204. In some embodiments, the merge manager 208 may be configured to merge the models 204 using multiple merge strategies 210 to generate multiple merge models 204. The merge manager 208 may be configured to select a merged model 204 from multiple results, for example, by receiving a selection of the best-merged model 204 from a technician.

To perform the merge, the merge manager 208 may be configured to align geometry of the models 204 based on a common point or other common location. The merge manager 208 is configured to select geometry from either of the models 204 using the merge strategy 210. The selected geometry is associated with a common anatomical location in the customer's dental arch. Selecting the geometry using the merge strategy 210 may include, for example, determining which of the dental impressions associated with the models 204 includes more detail associated with the common anatomical location and/or determining which of the models 204 includes greater depth associated with the common anatomical location. In some embodiments, the merge strategy 210 may include one or more of the steps described below with reference to FIG. 5-FIG. 10. The merge manager 208 may be further configured to clean (or smooth) the merged model 204 to generate a closed surface, for example, by performing Poisson surface reconstruction or by performing a gap closing (or smoothing) algorithm.

The impression manager 212 may be configured to obtain additional dental impressions if the input models 204 and/or the merged model 204 do not include a complete representation of the customer's dental arch. The manufacturing manager 214 may be configured to use the input models 204 and/or the merged model 204 for sculpting and setup or otherwise use the models 204 for manufacturing.

Figure 3:
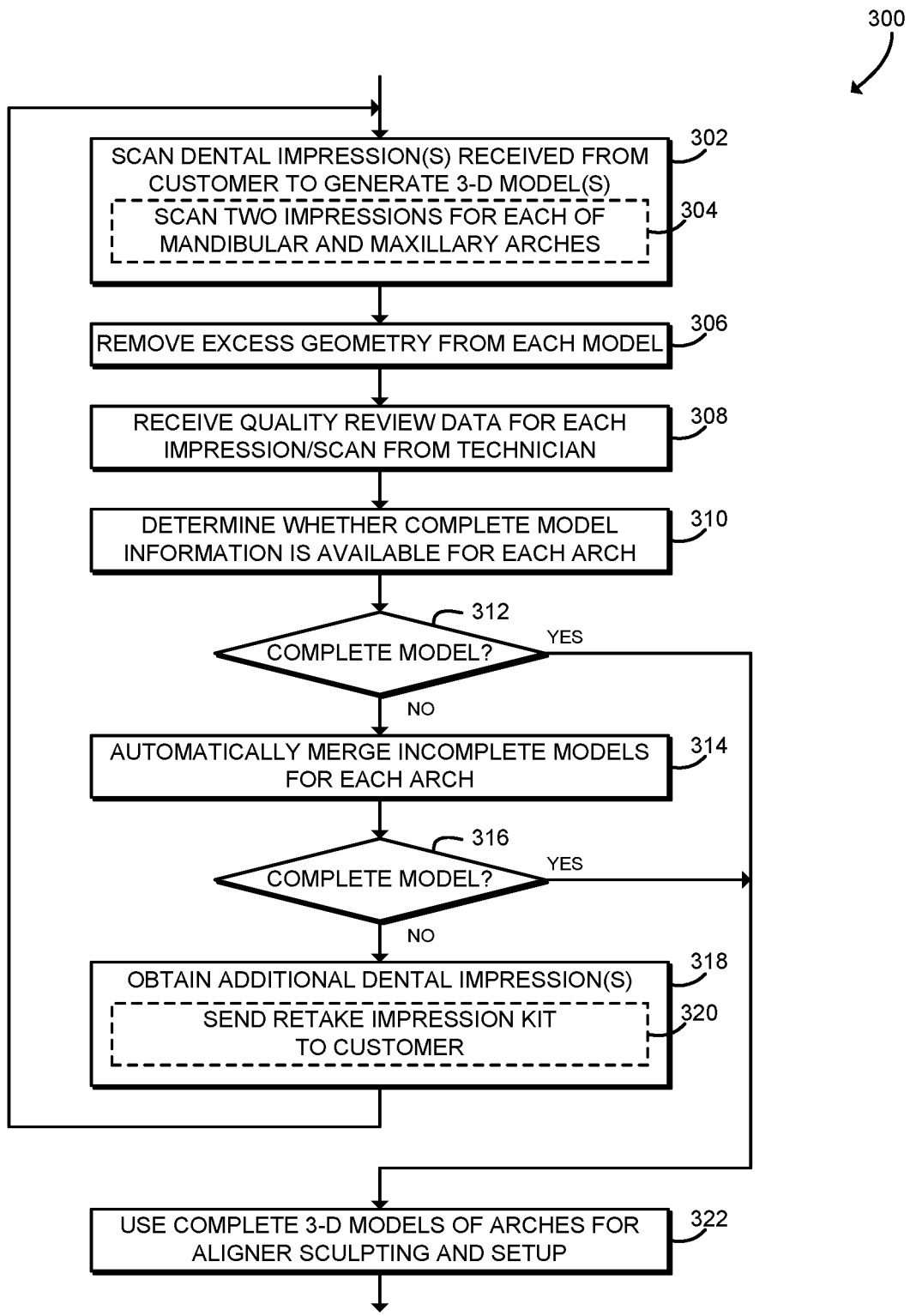
FIG. 3 is a flow diagram of at least one embodiment of a method for capturing and processing three-dimensional scans of dental impressions that may be executed by the computing device of FIGS. 1 and 2.

Referring now to FIG. 3, in use, the computing device 100 may execute a method 300 for capturing and processing three-dimensional scans of dental impressions. It should be appreciated that, in some embodiments, the operations of the method 300 may be performed by one or more components of the environment 200 of the computing device 100 as shown in FIG. 2. The method 300 begins in block 302, in which the computing device 100 scans one or more dental impressions received from a customer to generate three-dimensional models 204. The computing device 100 may use any stereoscopic imager, photometric scanner, laser scanner, infrared scanner, structured light sensor, or other three-dimensional scanning technology to scan the dental impressions. Each model 204 may be embodied as a three-dimensional representation of the geometry of a dental impression, which is in turn a negative representation of a dental arch (e.g., a mandibular arch or maxillary arch) of the customer. Illustratively, the models 204 are embodied as standard triangle language (STL) files that describe the surface geometry of the corresponding dental impressions. In other embodiments, the models 204 may be embodied as any surface or solid three-dimensional modeling data.

The computing device 100 may scan several impressions produced by the customer in connection with an at-home dental impression kit. For example, in some embodiments, in block 304, the computing device 100 may scan two impressions for each of the customer's mandibular arch (i.e., the customer's lower teeth) and the customer's maxillary arch (i.e., the customer's upper teeth), producing a total of four models 204. Additionally or alternatively, in some embodiments, the computing device 100 may scan a different number of dental impressions. For example, as described further below, a retake kit may include multiple dental impressions for one or more of the user's dental arches.

Additionally, although illustrated in FIG. 3 as scanning the dental impressions to generate the models 204, it should be understood that the computing device 100 may receive the models 204 from another device or otherwise acquire the models 204. For example, in some embodiments, the dental impressions may be scanned by a device located at a remote imaging lab, mobile imaging lab, or other remote location.

In block 306, the computing device 100 removes excess geometry from each model 204. The excess geometry may be removed, for example, by a technician using a 3-D editor, or may be removed automatically.

In block 308, the computing device 100 receives quality review data for each impression/scan from a technician. The technician may, for example, interactively view a representation of each model 204 and then provide the quality review data. The quality review data may indicate whether the corresponding dental impression includes a complete impression of the user's dental arch. Due to incorrect use by the customer or other factors, a dental impression may not include clear impressions of one or more teeth or other areas of a dental arch. Thus, in some embodiments, the quality review data may identify incomplete areas of each arch (e.g., incomplete sides, teeth, or other parts of the impression).

In block 310, for each of the mandibular arch and the maxillary arch, the computing device 100 determines whether one of the models 204 is complete. For example, the computing device 100 may determine whether any of the models 204 includes data for a complete impression of a dental arch using the quality review data. In block 312, the computing device 100 checks whether a model 204 is complete for both of the dental arches. If so, the method 300 branches ahead to block 322, described below. If a model 204 is not complete for either arch, the method 300 advances to block 314.

In block 314, for one or more of the dental arches, the computing device 100 automatically merges incomplete models 204 to generate a merged model 204. For example, the computing device 100 may merge two models 204 of the customer's mandibular arch and/or may merge two models 204 of the customer's maxillary arch. The computing device 100 may use one or more merge strategies 210 to select geometry from one of the models 204 and replace geometry in the other model 204 with the selected geometry. Thus, after merging, the merged model 204 may include geometry generated by scanning more than one physical object (e.g., from more than one dental impression). One potential embodiment of a method for automatically merging the models 204 is described below in connection with FIG. 4.

In block 316, for each of the mandibular arch and the maxillary arch, the computing device 100 checks whether one of the models 204, including the merged model 204, is complete. If so, the method 300 branches ahead to block 322, described below. If a model 204 is not complete, the method 300 advances to block 318.

In block 318, the computing device 100 obtains additional dental impressions for the incomplete dental arch(es). In some embodiments, in block 320 the computing device 100 may cause a retake impression kit to be sent to the customer. The retake impression kit may include materials (e.g., dental trays and thixotropic impression material) to create one or more dental impressions for the incomplete dental arch or arches. After obtaining additional dental impressions, the method 300 loops back to block 302, in which the additional dental impressions may be scanned, checked for completeness, and potentially merged with the existing models 204.

Referring back to block 316, if a model 204 is complete for both of the dental arches, then the method 300 advances to block 322, in which the computing device 100 uses the complete models 204 of the customer's dental arches to perform sculpting and setup. For example, a complete model 204 may be used to generate a three-dimensional treatment plan for the customer, to generate or manufacture a positive model of the customer's dental arches, and/or to manufacture invisible aligners for the customer. After using the complete models 204, the method 300 is completed. The method 300 may be executed again for an additional customer and/or for additional dental impressions.

Figure 4:
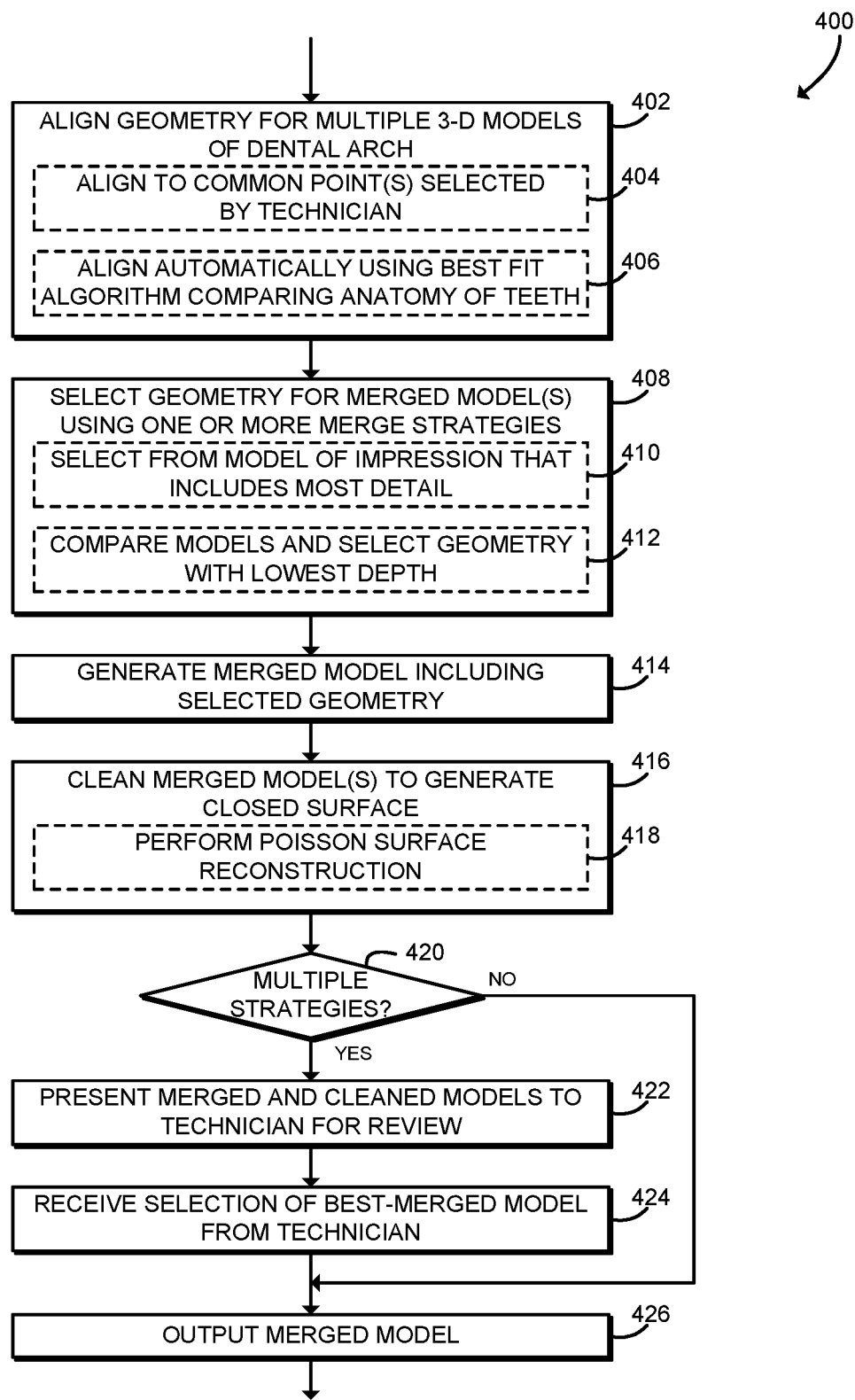
FIG. 4 is a flow diagram of at least one embodiment of a method for merging three-dimensional models that may be executed by the computing device of FIGS. 1 and 2.

Referring now to FIG. 4, in use, the computing device 100 may execute a method 400 for merging three-dimensional models. The method 400 may be executed in connection with block 314 of FIG. 3, as described above. It should be appreciated that, in some embodiments, the operations of the method 400 may be performed by one or more components of the environment 200 of the computing device 100 as shown in FIG. 2. The method 400 begins in block 402, in which the computing device 100 aligns the geometry of multiple models 204. Each of the models 204 may be generated from a scan of a dental impression of one of the customer's dental arches. For example, the computing device 100 may merge two models 204 associated with the mandibular arch of the customer or may merge two models 204 associated with the maxillary arch of the customer. The geometry of the models 204 is aligned according to the underlying geometry of the dental impressions and, therefore, the corresponding anatomy of the customer's dental arches. In some embodiments, in block 404 the models 204 may be aligned to one or more common points selected by a technician. For example, the technician may interactively identify teeth or other common features in each of the models 204. In some embodiments, in block 406 the models 204 may be aligned automatically using a best fit algorithm that compares the anatomy of the teeth represented in each of the models 204. One embodiment of aligning the models 204 is described below in connection with FIG. 11.

After aligning the geometry, in block 408 the computing device 100 selects geometry from the models 204 to include in a merged model 204 using one or more merge strategies 210. The computing device 100 may select geometry from a model 204 to fill in incomplete parts of the other model 204. In some embodiments, in block 410, the computing device 100 may select geometry from the model 204 corresponding to the dental impression that includes the most detail of the user's anatomy. For example, the computing device 100 may select geometry from a model 204 of a dental impression that captures the customer's anatomy from the tip of the teeth to the gingival line.

In some embodiments, in block 412 the computing device 100 may compare the models 204 and select geometry from the model 204 having the greatest depth. In other words, the computing device 100 may select geometry from the model 204 with the greatest distance from the bottom of the impression (e.g., corresponding to the tip of a tooth) up to the top of the impression (e.g., the surface of the impression mixture). For example, the computing device 100 may combine the models 204 into multiple layers, and then select lower points from the layers. Having lower depth in the model 204 indicates that the dental impression was also deeper, and deeper dental impressions tend to capture greater detail of the customer's tooth and gum anatomy.

Additionally, using the deeper model 204 may remove noise from the model 204, such as spikes in the impression caused by the impression mixture pulling up as the impression is removed from the customer's teeth.

In block 414, the computing device 100 generates the merged model 204 including the selected geometry. The merged model 204 may include 3D geometry from both of the models 204, with the less-detailed components of the geometry removed.

In block 416, the computing device 100 may clean the merged model 204 to generate a closed surface, also known as a watertight mesh. In some embodiments, the model 204 may be embodied as a mesh or other surface model, and that mesh may include holes or be otherwise open. Generating a closed surface may allow the merged model 204 to define a solid object that can, for example, be input to a 3-D printer. The computing device 100 may use any technique to clean the merged model 204. In some embodiments, in block 418 the computing device 100 may perform Poisson surface reconstruction to generate the closed surface. Additionally or alternatively, in some embodiments the computing device 100 may perform a gap closing algorithm for surface reconstruction to generate the closed surface.

In block 420, the computing device 100 determines whether multiple merge strategies 210 were used to generate multiple merged models 204. As described above in connection with block 408, the computing device 100 may use more than one merge strategy 210 to merge the models 204. Each merge strategy 210 may generate a different merged model 204. If a single merge strategy 210 is used, the method 400 branches ahead to block 426. If more than one merge strategy 210 is used, the method 400 advances to block 422.

In block 422, the computing device 100 presents the merged and cleaned models 204 generated using the multiple merge strategies 210 to a technician for review. In block 424, the computing device 100 receives a selection of a merged model 204 from the technician. The technician may, for example, manually select the best-merged model 204.

In block 426, the computing device 100 outputs the merged model 204. As described above in connection with FIG. 3, if the merged model 204 is complete, it may be used to prepare a three-dimensional treatment plan for the customer, to generate or manufacture a positive model of the customer's dental arches, to manufacture invisible aligners for the customer, or otherwise be used for dental treatment. After outputting the merged model 204, the method 400 is completed. The method 400 may be executed repeatedly to perform additional merges.

Figure 5:
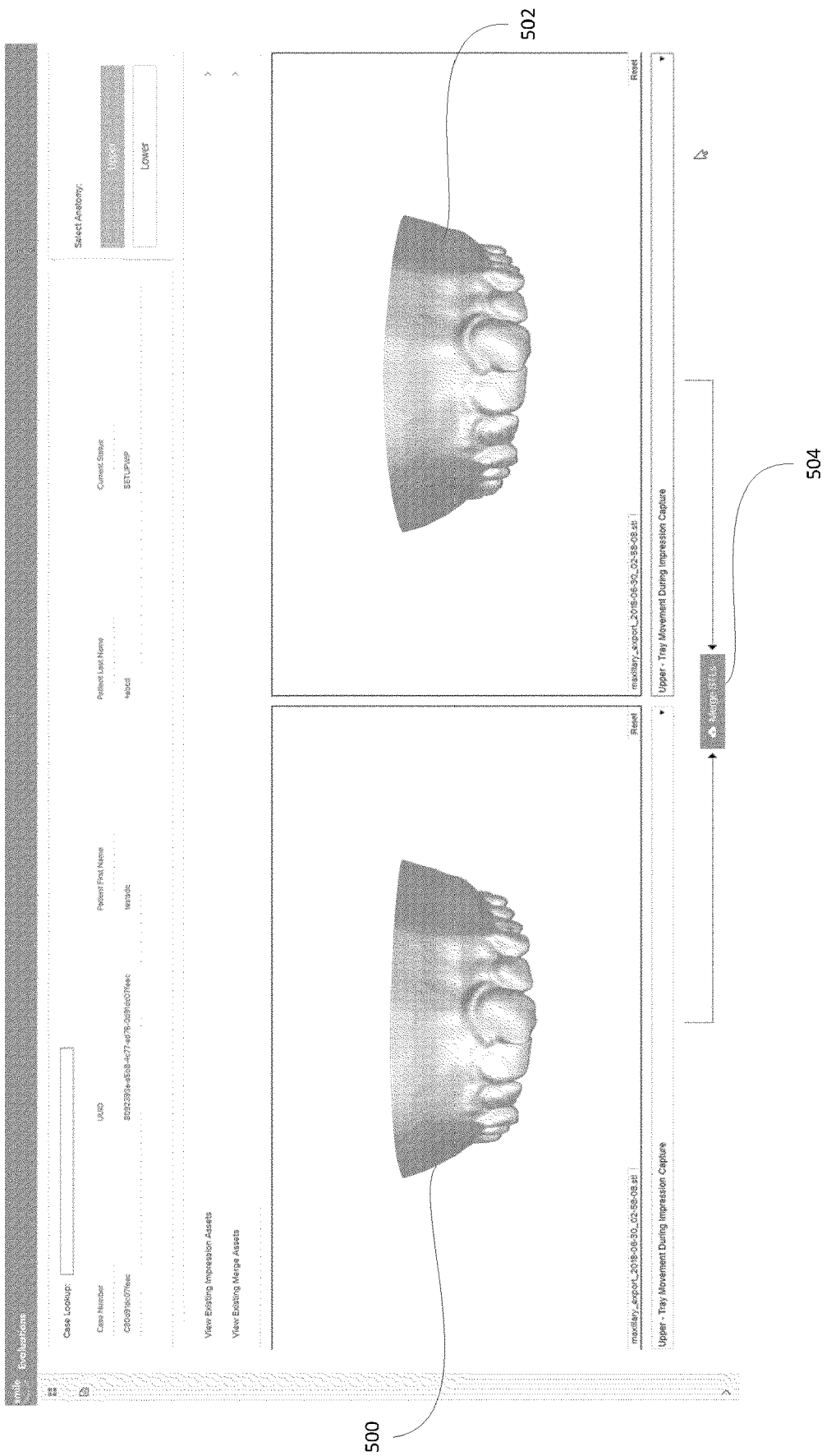
FIG. 5 is a user interface for uploading first and second models to be merged.
Figure 6:
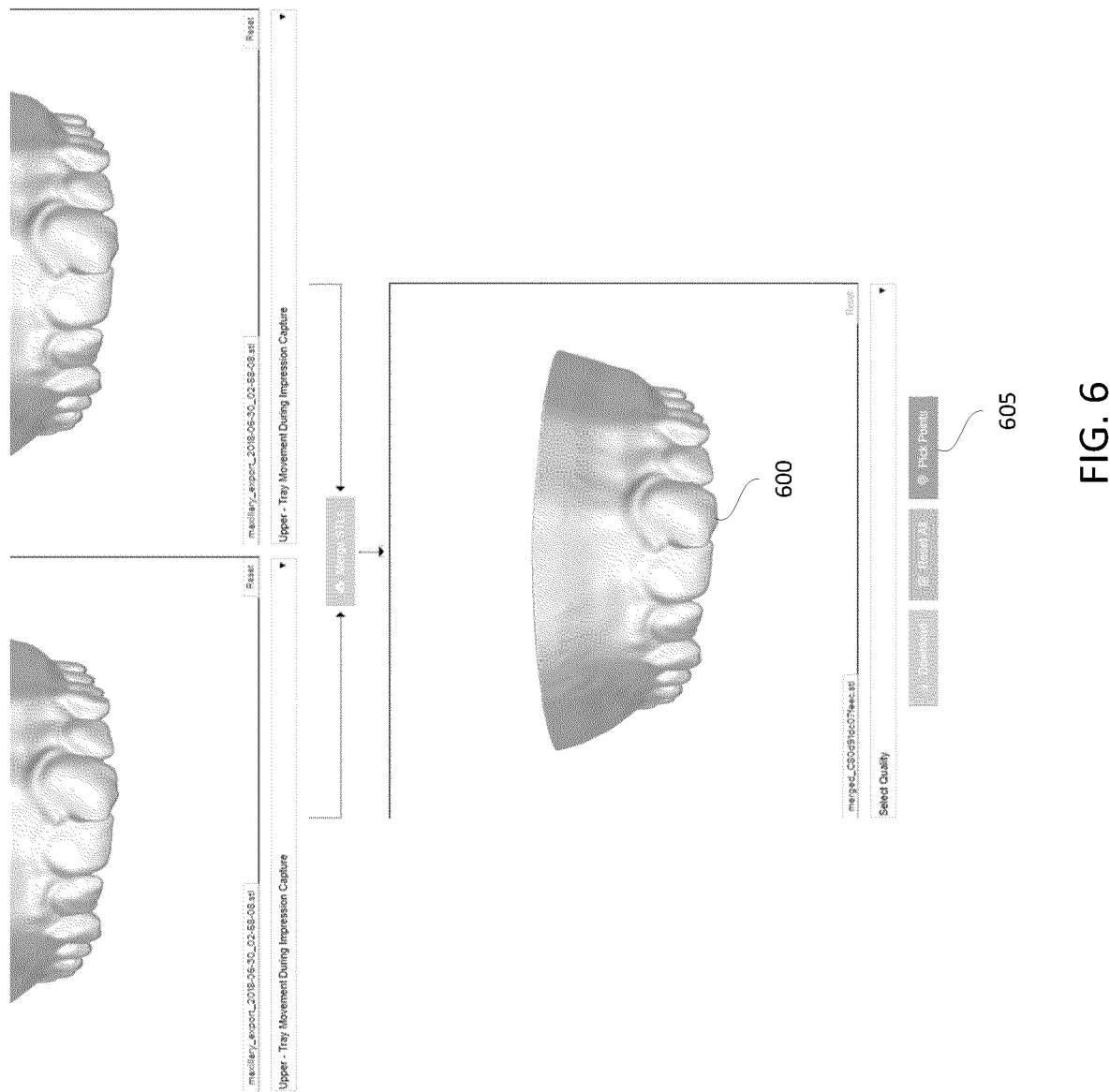
FIG. 6 is a user interface showing a rough merge of the first and second models of FIG. 5.
Figure 7:
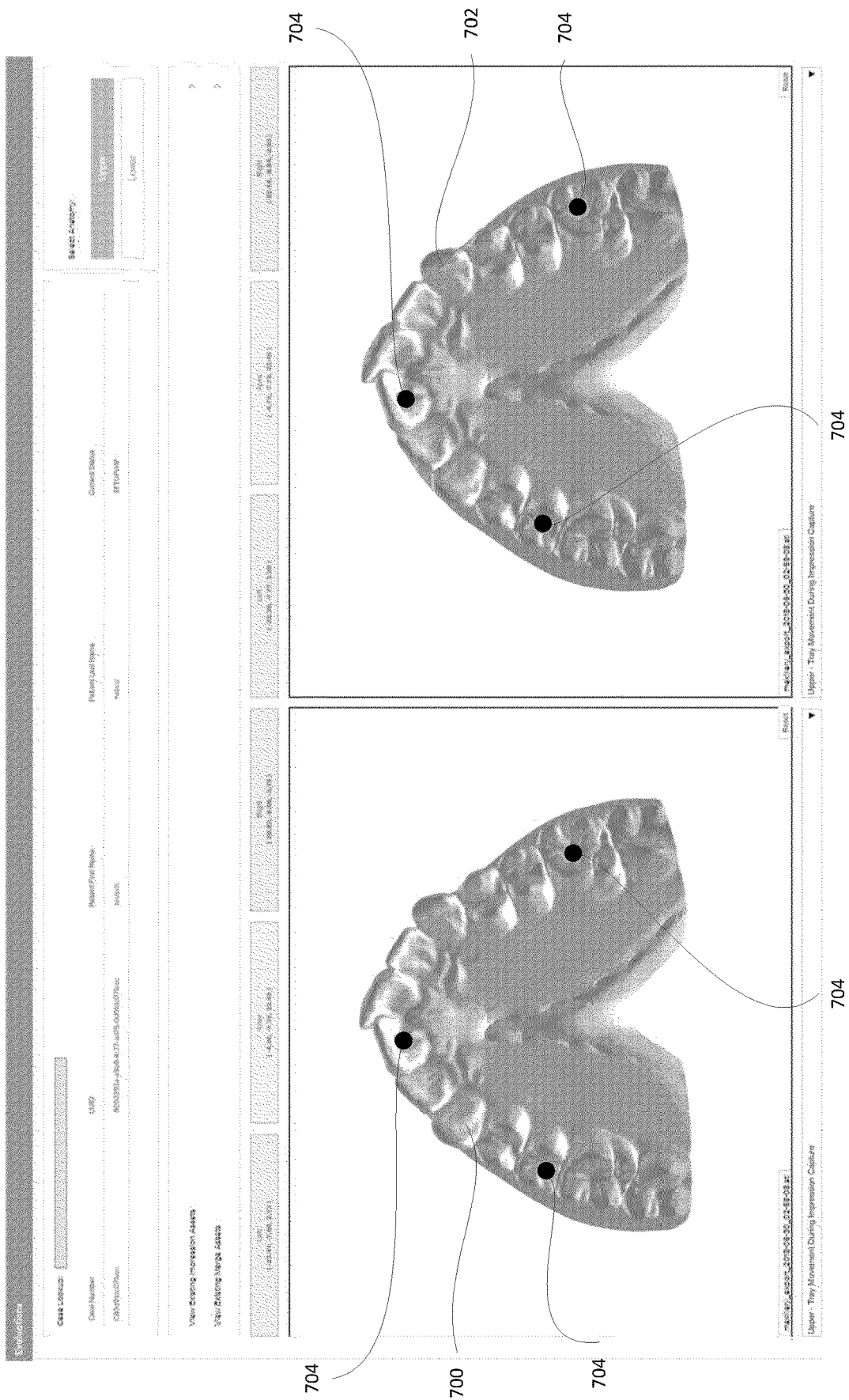
FIG. 7 is a user interface showing the occlusal surface of the first and second models of FIG. 5 for selecting correlation points in the two models.

Referring now to FIG. 5-FIG. 7, various user interfaces are shown for generating a merged model 204, according to exemplary embodiments. Specifically, FIGS. 5-7 depict a series of user interfaces which may be used for merging two or more models 204 to output a merged model 204. In some embodiments, the user interfaces may be operated, controlled, or otherwise used by a user of the computing device 100. In some embodiments, one or more of the steps outlined below may be automated (and thus the user interface corresponding to such steps may be omitted or modified).

FIG. 5 depicts a user interface for uploading models to be merged. The models may be represented in various file formats. For instance, the models may be represented as geometric faces coupled to one another according to a surface contour. In some embodiments, the geometric faces may be triangles (e.g., the file format may be STL). Each triangle may be joined at the sides by adjacent triangles proximate thereto. Hence, the triangles form a mesh which represents the surface contour or geometry of the user's mouth, or at least the user's teeth and gums (as captured by the dental impression or three-dimensional scan). As described above, the model manager 202 is configured to generate and store multiple models 204. Such models 204 may include a first model 500 and a second model 502. The first model 500 and second model 502 are representations of the same dental arch of a user. For example, the first model 500 can be captured at a first time and the second model 502 can be captured at a second time (e.g., shortly after the first model 500 is captured).

In some embodiments, a user uploads the first model 500 and second model 502 to the computing device 100 (e.g., for use by the model manager 202). The user may select or otherwise provide an address to a file location corresponding to the first and second models 500, 502, drag and drop the files corresponding to the models 500, 502 into a workspace, a file upload box, or other user interface element which may be used for uploading files to the computing device 100. In some embodiments, the model manager 202 automatically retrieves the first and second models 500, 502 (e.g., based on a creation time, based on a file name, etc.). In each of these embodiments, the model manager 202 receives, acquires, obtains, or otherwise generates and includes the first model 500 and second model 502.

The user may select (or the model manager 202 may automatically initiate) a merge model option 504. The merge model option 504 is shown to be represented as a button ("Merge STLs") on the user interface, though the merge model option 504 may be implemented in other ways via the user interface.

Upon selection and/or initiation of the merge model option 504, the merge manager 208 may be configured to generate a rough merge 600 of the model. FIG. 6 shows a rough merge of the first and second models 500, 502, according to an exemplary embodiment. The merge manager 208 may generate the rough merge 600 in a number of ways. The merge manager 208 may identify, estimate, etc., corresponding anatomical features between the first model 500 and second model 502. For instance, the merge manager 208 may match crowns in the first model 500 with crowns in the second model 502. The user is then prompted to select correlation points for generating a more accurate merge than the rough merge 600, or for modifying the rough merge 600 prior to generating the more accurate merge. A select points option 605 is shown on the user interface. While the select points option 605 is shown to be represented on the user interface as a button, the select points option 605 may be implemented in other ways via the user interface. Upon the select points option 605 being selected by the user, the user may be prompted to select correlation points between the two models 500, 502 for refining the merged model, as described in greater detail below.

Following the merge model option 504 being initiated (e.g., by the user or by the model manager 202), various corresponding points for the first and second models 500, 502 are selected for aligning the models 500, 502. The user interface shown in FIG. 7 depicts the occlusal surface 700, 702 of the first and second models 500, 502, respectively, for selecting correlation points 704 in the two models 500, 502. The correlation points 704 include a left point, an apex point, and a right point for each model 500, 502. The left correlation point 704 on the first model 500 may be a point on the left side of the first model 500 which correlates or corresponds to a correlation point 704 on the left side of the second model 502. Similarly, the apex correlation point may be a point towards the center of the first model 500 which correlates to a correlation point 704 towards the center of the second model 502, and the right correlation point 704 on the first model 500 may be a point on the right side of the first model 500 that correlates to a correlation point 704 on the right side of the second model 502. In some embodiments, a user selects the correlation points 704, for instance, by locating a geometric feature on the first model 500, selecting that geometric feature on the first model 500, and locating and selecting a similar, related, or corresponding geometric feature on the second model 502. In some embodiments, the merge manager 208 selects the correlation points 704 (e.g., based on correlating geometric features in the respective models 500, 502). In each embodiment, a user may modify the location of the correlation points 704 based on the prominence of geometric features in the first and second models 500, 502 to better align the first and second models 500, 502. The user may select the correlation points 704 and drag the selected correlation points 704 to different locations as needed.

Once the correlation points 704 on the first model 500 and second model 502 are selected, the first and second models 500, 502 are merged. The merge manager 208 is configured to merge the first model 500 and second model 502.

Figure 8:
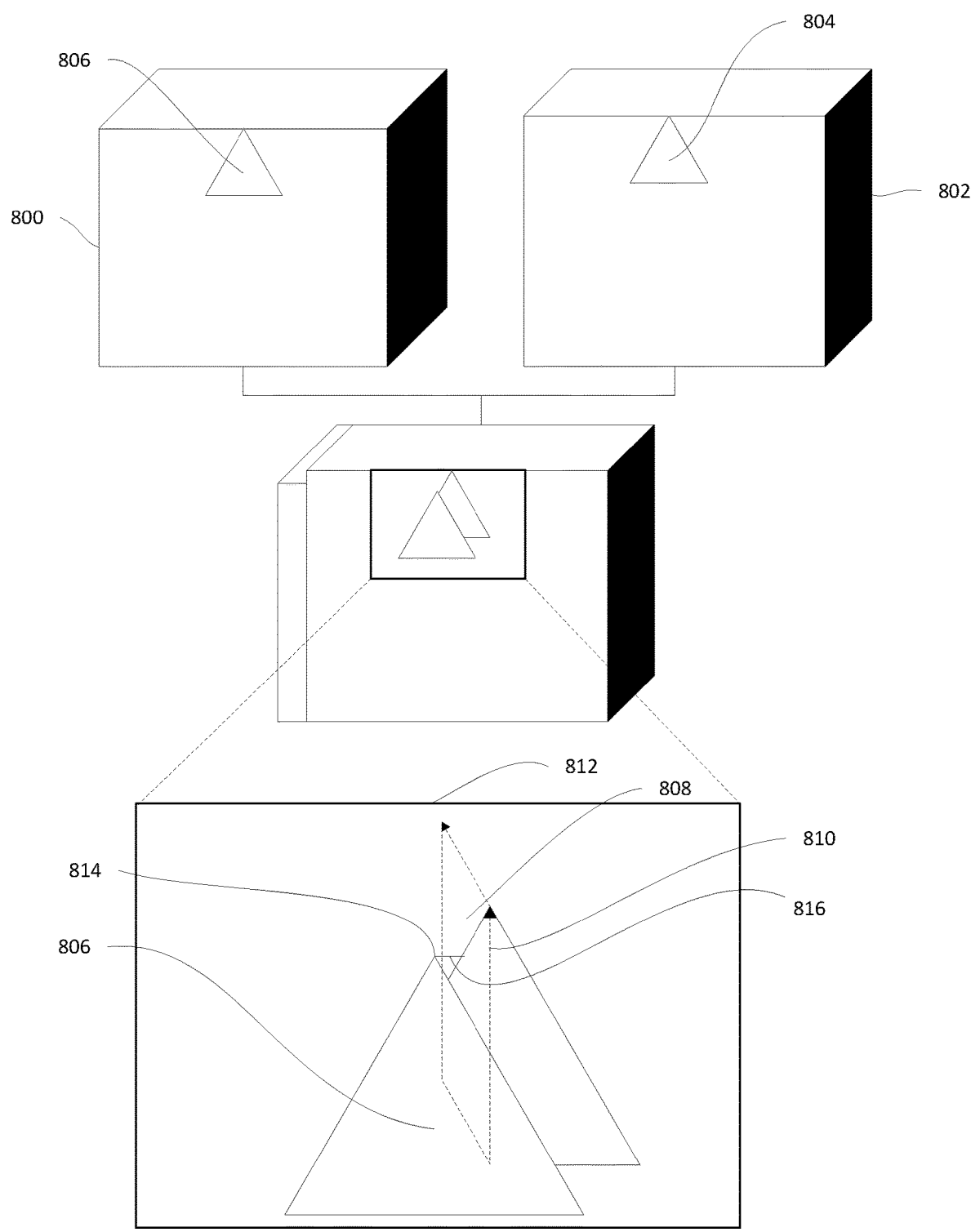
FIG. 8 is a simplified representation of two three-dimensional models being merged.

Referring now to FIG. 8, in some embodiments, the merge manager 208 is configured to align the occlusal surface 700 of the first model 500 with the occlusal surface 702 of the second model 502. Specifically, FIG. 8 shows simplified first and second models 800, 802 which are merged to form a merged model 900 (of FIG. 9). In some embodiments, the merge manager 208 overlays the correlation points 704 for the first model 500 and the correlation points 704 for the second model 502 to align the first model 500 and second model 500. As the merge manager overlays the correlation points 704 for the first model 500 and the correlation points 704 for the second model 502, each of the geometric faces for the first model 500 are overlaid on the second model 502. As such, the first model 500 is stacked on top of and aligned with the second model 502. Where the models 500, 502 are the same, each of the geometric faces on the first and second models may be aligned with corresponding geometric faces and extend within the same plane. Where the models 500, 502 deviate from one another, at least some of the geometric faces may not be aligned, or may not extend within the same plane. Hence, some geometric faces in the first model 500 may be offset from corresponding geometric faces in the second model 502. The merge manager 208 is configured to apply various best fit calculations, which compare the anatomy of the scanned teeth, to more finely align the first and second models 500, 502.

As shown in FIG. 8, and in some embodiments, the merge manager 208 is configured to determine whether a geometric face 804 of the second model 802 has a depth greater than a geometric face 806 of the first model 800. As can be seen in FIG. 8, the first model 800 has different dimensions from the dimensions of the second model 802. As such, the geometric faces 804, 806 are not aligned and does not extend within the same plane.

The merge manager 208 is configured to selectively remove geometric faces from the first and/or second model. The merge manager 208 is configured to selectively remove geometric faces from the first and/or second model based on relative depth of the geometric faces. In some embodiments, the merge manager 208 identifies corresponding geometric faces for the first and second models 500, 502. For instance, when the first model 500 is stacked atop and aligned with the second model 502, the merge manager 208 may identify the nearest geometric faces for the first and second models 500, 502. Where the models 500, 502 are the same, for a given geometric face for the first model 500, the nearest geometric face on the second model 502 is aligned and extends in the same plane. At locations where the first and second models 500, 502 are not the same, corresponding geometric faces for the first model 500 and second model 502 will be slightly offset from one another.

The merge manager 208 may be configured to identify, for a given geometric face of the first model 500, a corresponding geometric face on the second model 502 which is nearest to the geometric face of the first model 500. The merge manager 208 may be configured to identify the nearest face on the second model 502 for each geometric face on the first model 500.

As shown in FIG. 8, the geometric face 806 for the first model 800 and the geometric face 804 for the second model 802 are offset. The merge manager 208 may quantify the offset for the geometric faces 804, 806 for determining whether one of the first and second geometric faces 804, 806 have a greater depth. The merge manager 208 is shown in FIG. 8 to define a plane 808 on the second model 802. In some embodiments, the merger manager 208 defines a plane 808 within or corresponding to the geometric face 804 nearest to the geometric face 806 on the first model 800. The merge manager 208 may identify a vertex 810 for the geometric face 804. The vertex 810 may be the peak (or maximum elevation) of the geometric face 804. The merge manager 208 may define the plane 808 based on the vertex 810. In some embodiments, the merge manager 208 defines the plane 808 based on the identified vertex 810 and a normal vector 812 (e.g., a perpendicularly extending vector with respect to the vertex 810) for the vertex 810. Hence, the plane 808 in these embodiments extends perpendicularly from the geometric face 804 and is aligned with the vertex 810.

In some embodiments, the merge manager 208 is configured to identify a vertex 814 for the geometric face 806 of the first model 800 (e.g., the geometric face 806 nearest to the geometric face 804). Similar to the vertex 810 of the second model 802, the vertex 814 of the first model 800 may be the peak (or maximum elevation) of the geometric face 806.

The merge manager 208 is configured to determine a distance 816 between the vertex 814 and the plane 808. The distance 816 may correspond to the offset between the geometric faces 804, 806. In some embodiments, the distance includes X, Y, and Z components (e.g., height, width, and depth). The merge manager 208 may be used for determining relative depth of the first and second models 500, 502. In some embodiments, the merge manager 208 compares the distance 816 between the vertex 814 and plane 808 to a threshold. The threshold may correspond to a relative depth between the geometric faces 804, 806 corresponding to one another. In some embodiments, the threshold is a minimum distance. The distance 816 may satisfy the threshold when the distance 816 exceeds the minimum distance. In other embodiments, the threshold is between a minimum and maximum distance. Thus, the distance 816 may satisfy the threshold when the distance 816 falls between the minimum and maximum distance of the threshold.

The merge manager 208 is configured to remove geometric faces on a given model where a corresponding geometric face on the other model has a greater depth. For instance, the merge manager 208 may remove the geometric face 806 on the first model 800 where the geometric face 804 on the second model 802 has a greater depth (e.g., with respect to the geometric face 806). In some embodiments, where the distance 816 satisfies the threshold, the merge manager 208 may remove the geometric face 802 on the first model 800.

In some embodiments, the merge manager 208 is configured to identify the relative depth by casting a ray from each face on the first model 500 to nearby faces on the second model 502. The merge manager 208 may cast a ray for each geometric face in the first model 500 to nearby faces on the second model 502. The merge manager 208 may define a reverse face normal plane or vector (e.g., a plane extending beneath and perpendicular) for a geometric face on the first model 500. The merge manager 208 may cast the ray from the reverse face normal plane or vector towards the nearby geometric faces in the second model 502. The merge manager 208 may determine whether any geometric faces on the second model 502 intersect with the ray (within a tolerance or threshold, for instance). Where a face on the second model 502 intersects with the ray, the merge manager 208 removes the geometric face on the second model 502.

The merge manager 208 may be configured to identify, determine, and/or quantify a depth between relative geometric faces for each of the geometric faces of the first model 500. Hence, the merge manager 208 may evaluate each of the geometric faces of the first model 500, and at least some of those geometric faces may be removed. In some embodiments, the merge manager 208 may be configured to re-execute the steps outlined above with the first and second models 500, 502 reversed (e.g., where the second model 502 is stacked atop and aligned with the first model 500). The merge manager 208 identifies nearest geometric faces on the first model 500 for a given geometric face on the second model 502, defines a plane for the first model, and identifies a distance between the plane and a vertex of the geometric face on the second model.

In some embodiments, the merge manager 208 identifies geometric face(s) which are isolated in a geometric model 500, 502 (e.g., a given geometric face is surrounded by voids where geometric faces were removed). The merge manager 208 may delete isolated geometric face(s).

Following such processing of the geometric models, the merge manager 208 is configured to select a geometry. The selected geometry may be or include a selection of the first or second models 500, 502. The selected geometry may include the geometric faces remaining after removal of some of the geometric faces based on corresponding depth. The merge manager 208 may select a geometry from the first and second models 500, 502 based on remaining surface area, number of geometric faces remaining in each model 500, 502, etc. The selected geometry may be used for forming the merged model. In some embodiments, the merge manager 208 incorporates, or combines, geometric faces from the unselected geometry into the selected geometry (e.g., to fill gaps or voids within the selected geometry). The merge manager 208 may process the selected geometry to fill the gaps or voids. In some embodiments, the merge manager 208 applies a smoothing function to the merged model. The merge manager 208 may be further configured to clean or smooth the merged model to generate a closed surface, for example, by performing Poisson surface reconstruction or by performing a gap closing or smoothing algorithm.

Figure 9:
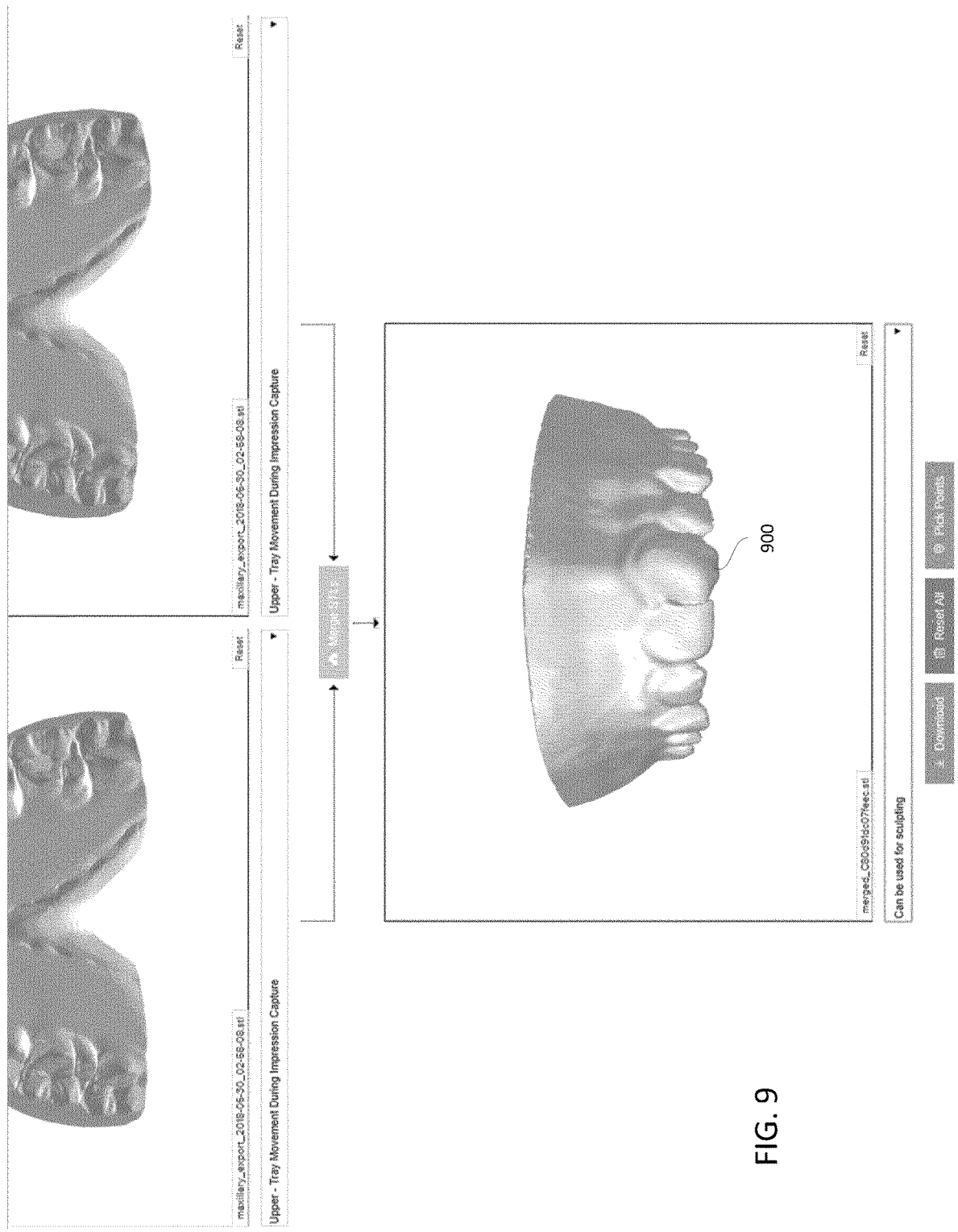
FIG. 9 is a user interface depicting the merged model generated from the first and second models.

The merge manager 208 may be configured to render the merged model to a user, such as a dental technician, via a user interface. FIG. 9 shows a user interface depicting the merged model 900 generated from the first and second models 500, 502. In some embodiments, the merge manager 208 merges the first and second models 500, 502 according to a number of different merge strategies. The merge manager 208 may merge the first and second models 500, 502 according to merge strategies that address shifted scans, improper dental impression material mixtures, etc. The merge manager 208 may be configured to automatically select the best merging strategy using, for instance, artificial intelligence, machine learning, neural networks, etc. The merge manager 208 may, for instance, train a neural network for identifying which merging strategies result in the best merged model.

In some embodiments, the merge manager 208 is configured to display each of the merged models 900 to a user, such as a technician, on a display or the user interface as shown in FIG. 9. In some embodiments, the user interface includes an image of the patient's smile (e.g., corresponding to the dental impression). The image may be displayed side-by-side with the merged model (and, optionally, the first and second models 500, 502). The technician may select the ideal merged model based on the side-by-side photo. Following selection of the merged model for use, the technician may manipulate, modify, etc. the merged model to reposition the patient's teeth, and the technician may export the modified merged model to the manufacturing manager 214 for manufacturing dental aligners for repositioning the patient's teeth, as described above.

Figure 10:
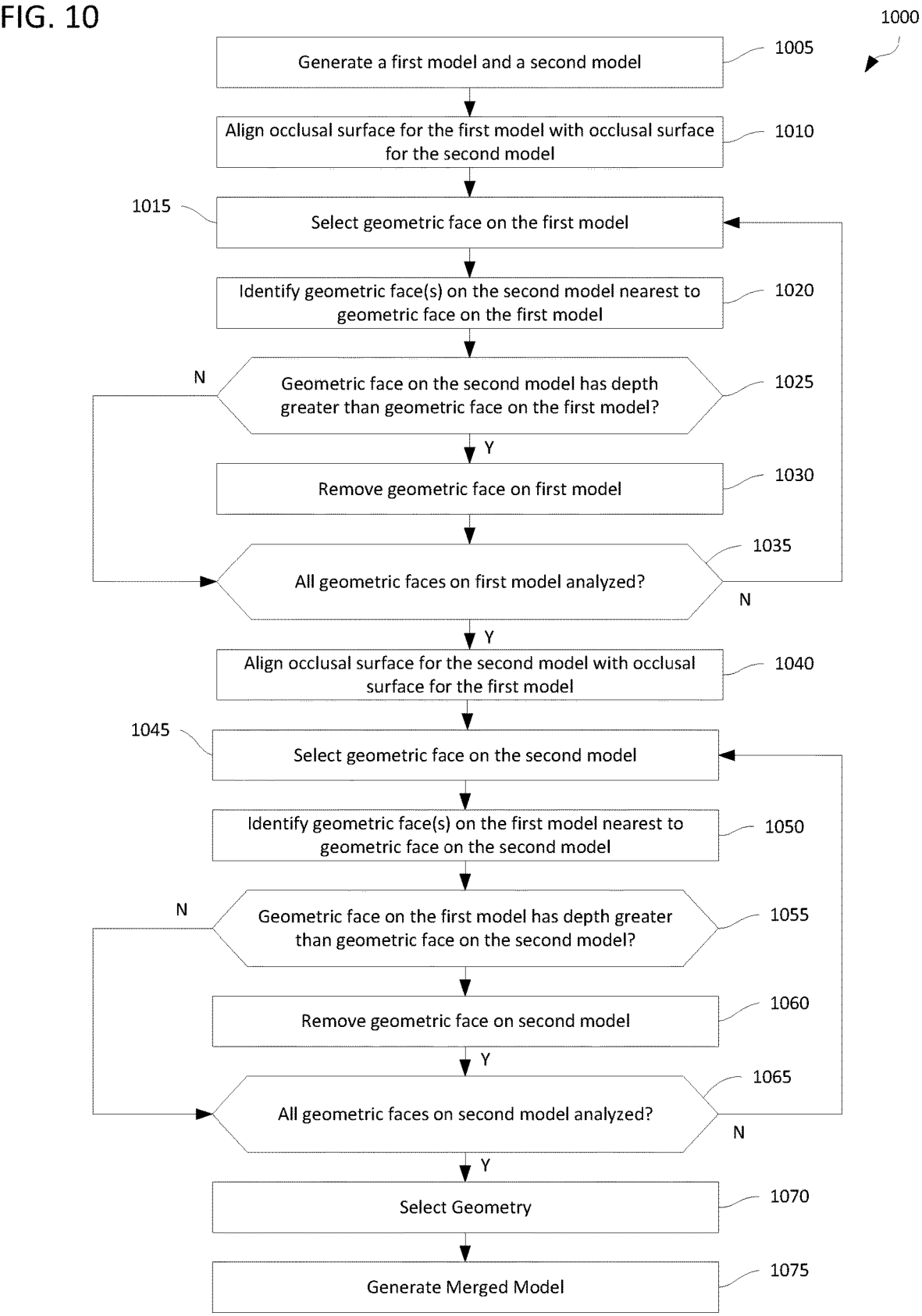
FIG. 10 is a flow diagram of at least one embodiment of another method of merging three-dimensional models that may be executed by the computing device of FIGS. 1 and 2.

Referring to FIG. 10, a flowchart depicting one embodiment of a method 1000 for dental impression scan merging is shown, according to an exemplary embodiment. Similar to FIG. 3, it should be appreciated that, in some embodiments, the operations of the method 1000 may be performed by one or more components of the environment 200 of the computing device 100 shown in FIG. 2.

At step 1005, the computing device 100 generates a first model and second model. In some embodiments, the computing device 100 scans one or more dental impressions received from a customer to generate three-dimensional models 204. Hence, the first model may be a three-dimensional model including a plurality of geometric faces indicative of a first dental impression of a user's dental arch, and the second model may be a three-dimensional model including a plurality of geometric faces indicative of a second dental impression of the user's dental arch (e.g., the same dental arch). The computing device 100 may use any stereoscopic imager, photometric scanner, laser scanner, infrared scanner, structured light sensor, or other three-dimensional scanning technology to scan the dental impressions. Each model 204 may be embodied as a three-dimensional representation of the geometry of a dental impression, which is in turn a negative representation of a dental arch (e.g., a mandibular arch or maxillary arch) of the customer. Illustratively, the models 204 are embodied as STL files that describe the surface geometry of the corresponding dental impressions and include geometric faces which form a mesh which defines the surface geometry or contours. In other embodiments, the models 204 may be embodied as any surface or solid three-dimensional modeling data.

At step 1010, and in some embodiments, the computing device 100 aligns an occlusal surface 700 of the first model 500 with an occlusal surface 702 of the second model 502. In some embodiments, the computing device 100 analyzes geometric properties of the first and second models 500, 502 for aligning the occlusal surfaces 700, 702. In some embodiments, the computing device 100 receives or automatically selects correlation points 704 on the first and second models 500, 502. The computing device 100 may overlay the correlation points 704 and remaining portions of the first and second models 500, 502. The computing device 100 may align the occlusal surfaces 700, 702 such that at least some of the geometric faces in the first and second models 500, 502 are aligned and extend in the same plane. Where the first and second models 500, 502 are different from one another, the geometric faces may be offset from one another. For instance, some geometric faces on one model may correspond to greater measured or captured depths than in the other model.

At step 1015, and in some embodiments, the computing device 100 selects a geometric face on the first model 500. The computing device 100 may progressively select geometric faces on the first model 500 beginning in one area (e.g., the right side, the center or apex, etc.), and progress through the geometric faces in the first model 500, as described in greater detail below.

At step 1020, and in some embodiments, the computing device 100 identifies a geometric face on the second model 502 nearest to the geometric face selected at step 1015. In embodiments where the first and second models 500, 502 are the same, the nearest geometric face on the second model 502 is directly aligned with and extends planar to the geometric face selected at step 1015. In embodiments where the models 500, 502 are not the same, the identified geometric face on the second model 502 nearest to the geometric face selected at step 1015 may be slightly offset from one another.

At step 1025, and in some embodiments, the computing device 100 may determine whether the geometric face on the second model 502 has a depth greater than the geometric face on the first model 500. In some embodiments, the computing device 100 may define a plane on the second model 500. Specifically, the computing device 100 defines a plane on the geometric face on the second model 500. The plane may extend along the vertex for the geometric face and a normal vector for the vertex. Hence, the plane may extend outwardly from (e.g., perpendicularly to) and along the vertex of the geometric face. The computing device 100 may determine a distance between the vertex of the geometric face on the first model 500 and the plane. The computing device 100 may compare the distance to a threshold (e.g., a minimum distance, a range of distances, etc.). In some embodiments, the merge manager 208 identifies the relative depth by casting a ray from the geometric face on the first model 500 to the geometric face on the second model 502. The computing device 100 may define a reverse face normal plane or vector (e.g., a plane extending beneath and perpendicular) from the geometric face on the first model 500. The computing device 100 may cast a ray from the reverse face normal plane or vector to the geometric face on the second model 502. The merge manager 208 may determine whether the geometric face on the second model 502 intersects with the ray (e.g., within a tolerance or threshold, for instance). Where the geometric face on the second model 502 intersects with the ray, the computing device 100 may determine that the geometric face on the second model 502 has a greater depth.

Where the computing device 100 determines that the geometric face on the second model 502 has a depth greater than the geometric face on the first model 500, the method 1000 proceeds to step 1030. Where the computing device 100 determines that the geometric face on the second model 502 does not have a depth greater than the geometric face on the first model 500 (or the distance or depth do not satisfy a threshold), the method 1000 proceeds to step 1035.

At step 1030, and in some embodiments, the computing device 100 removes the geometric face on the first model 500. The computing device 100 may remove the geometric face on the first model 500 when the corresponding geometric face on the second model 502 has a greater depth. The computing device 100 may remove the geometric face on the first model 500 when the distance between the plane on the second model 502 and the vertex of the first model 500 satisfies a threshold (e.g., the vertex is greater than a minimum distance, falls within a range of distances, etc.) corresponding to relative depth. The computing device 100 may remove the geometric face on the first model 500 when the ray cast from a reverse face plane or vector intersects with the geometric face on the second model 502.

At step 1035, the computing device 100 may determine whether all geometric faces on the first model 500 have been analyzed. The computing device 100 may maintain a data log of each geometric face as the relative depth between the geometric face of the first and second models 500, 502 are determined. Where the computing device 100 determines that all geometric faces on the first model 500 have been analyzed, the method 1000 may proceed to step 1040. Where geometric faces have not been analyzed, the method 1000 may proceed back to step 1015, e.g., where the computing device 100 selects another geometric face of the first model 500. Hence, the method may loop between step 1015-1035 until all geometric faces of the first model 500 are analyzed.

At step 1040, the computing device 100 aligns the occlusal surface 702 of the second model 502 with the occlusal surface 700 of the first model 500. Following alignment, the second model and first model 500, 502 are reversed (e.g., with respect to the orientation at step 1010). In this regard, the first and second models 500, 502 are flipped. The first and second models 500, 502 are aligned, except that the second model 502 is on top of the first model 500 at step 1040. Following step 1040, the method 1000 may proceed to steps 1045-1065, which are similar to steps 1015-1035 described above.

Following analysis of each of the geometric faces on the second model (e.g., step 1065), the method 1000 proceeds to step 1070. At step 1070, the computing device 100 selects a geometry. The selected geometry may be or include a selection of the first or second models 500, 502. The selected geometry may include the geometric faces remaining after removal of some of the geometric faces based on corresponding depth. The computing device 100 may select a geometry from the first and second models 500, 502 based on remaining surface area, number of geometric faces remaining in each model 500, 502, etc. The selected geometry may be used for forming the merged model.

At step 1075, and in some embodiments, the computing device 100 generates the merged model. The computing device 100 may combine remaining geometric faces from the first and/or second model 500, 502 into the selected geometry. In some embodiments, the computing device 100 incorporates, or combines, geometric faces from the unselected geometry into the selected geometry (e.g., to fill gaps or voids within the selected geometry). The computing device 100 may process the selected geometry to fill the gaps or voids. In some embodiments, the computing device 100 applies a smoothing function to the merged model. The computing device 100 may be further configured to clean or smooth the merged model to generate a closed surface, for example, by performing Poisson surface reconstruction or by performing a gap closing or smoothing algorithm.

Figure 11:
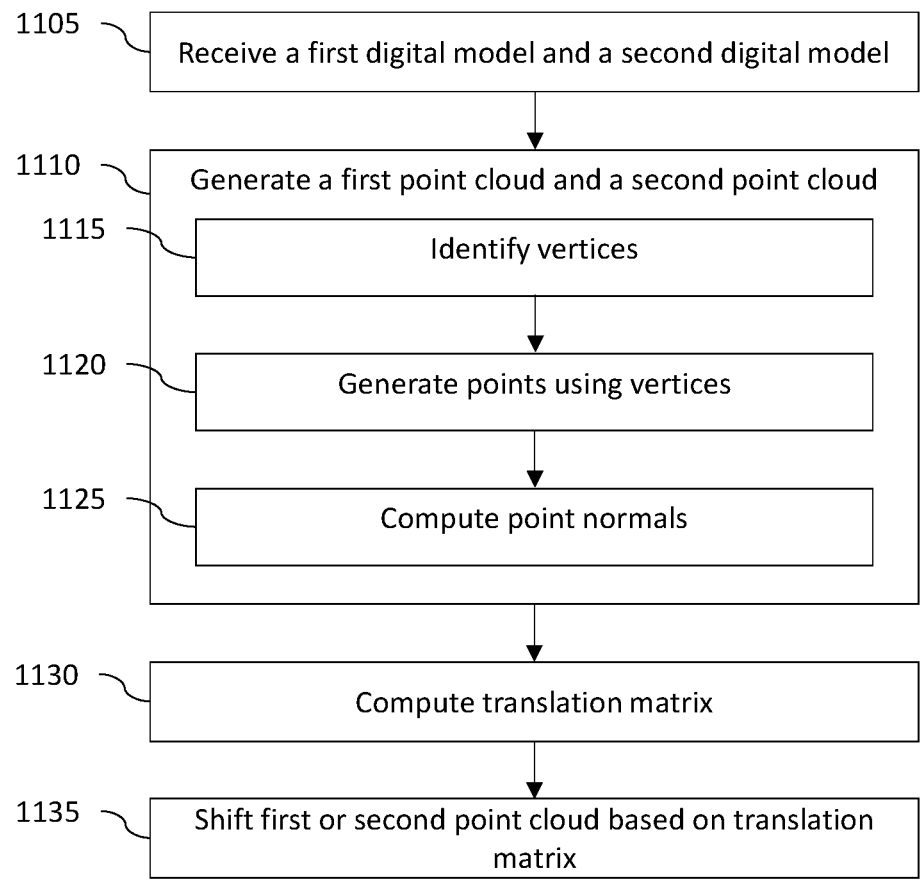
FIG. 11 is a flow diagram of at least one embodiment of a method of aligning two or more dental models that may be executed by the computing device of FIGS. 1 and 2.

Referring now to FIG. 11, a flowchart depicting one embodiment of a method 1100 for aligning two or more dental models is shown, according to an exemplary embodiment. Similar to FIG. 3, it should be appreciated that, in some embodiments, the operations of the method 1100 may be performed by one or more components of the environment 200 of the computing device 100 shown in FIG. 2. For instance, the steps depicted in method 1100 may be performed by the computing device 100.

At step 1105, the computing device 100 receives a first digital model and a second digital model. In some implementations, the first digital model and second digital model are generated based on a scan of two or more physical dental models of the same dental arch of a user, dental impressions of the same dental arch of a user, two or more scans of the same dental arch of a user, etc. Hence, the first digital model and second digital model are digital models of a common dental arch of a user (e.g., an upper arch or a lower arch of the same user). The computing device 100 may receive the first digital model and second digital model from a three-dimensional (3D) scanner. The digital models may be similar to the models described above with reference to FIG. 3. The computing device 100 may receive the digital models from any form or type of 3D scanner including, for instance a stereoscopic imager, photometric scanner, laser scanner, infrared scanner, structured light sensor, or other three-dimensional scanning technology configured to scan the dental impressions. Each model may be embodied as a three-dimensional representation of the geometry of a dental impression, which is in turn a negative representation of a dental arch (e.g., a mandibular arch or maxillary arch) of the user. Illustratively, the models are embodied as standard triangle language (STL) files that describe the surface geometry of the corresponding dental impressions. The STL files include a plurality of interconnected triangles having three vertices coupled to other triangles which, together, define, characterize, or otherwise describe the surface geometry of the customer's dental arch.

At step 1110, the computing device 100 generates a first point cloud and a second point cloud. In some implementations, the model manager 202 of the computing device 100 generates the first point cloud and the second point cloud. The model manager 202 generates a first point cloud for the first digital model, and a second point cloud for the second digital model. Each point cloud may include a plurality of points in a three-dimensional space which represent an outermost point on the surface of the user's dentition. The points of the point cloud may include a respective point normal. Each point normal includes a vector extending outwardly from the points of the point cloud. For each point, the vectors can be perpendicular to the surface of the digital model at the point. Each of the points and point normals for the point clouds may together define, characterize or otherwise describe the surface geometry of the customer's dental arch. The model manager 202 computes, determines, or otherwise generates the point clouds according to steps 1115-1125 described below. In some implementations, the model manager 202 may use, implement, or otherwise access one or more external systems, devices, or libraries, such as a TriMesh library, for determining, identifying, or otherwise generating one or more aspects of the point clouds.

At step 1115, the computing device 100 identifies each of the vertices of the geometric faces. In some implementations, the model manager 202 identifies vertices which connect two or more geometric faces. Where each of the geometric faces are triangles, the vertices are defined as the point in which two edges of the triangles meet. The model manager 202 parses each of the STL files for the first and second digital models to identify the vertices for each digital model. The model manager 202 may identify each geometric face, and correspondingly determine the vertices for those geometric faces. The model manager 202 may identify coordinates for each of the identified vertices (e.g., within the 3D space in which the digital models are generated). The model manager 202 may remove duplicate coordinates (e.g., vertices for adjacent geometric faces which share a common vertex).

At step 1120, the computing device 100 generates points using the vertices (e.g., identified at step 1115). In some implementations, the model manager 202 generates the points using each of the vertices of the geometric faces of the first and second models. The model manager 202 generates points for the point clouds which represent the respective model (e.g., a first set of points for the first point cloud representing the first digital model, a second set of points for a second point cloud which represents the second digital model, etc.). The model manager 202 may generate the points using the coordinates of the vertices of the geometric faces of the first and second models. In the 3D space, each point may be located on a vertex for a geometric face of the digital model that corresponds to the STL file.

In some implementations, the model manager 202 may generate the points using a subset of the coordinates of the vertices. In this regard, the model manager 202 may be configured to down-sample the vertices to down-sample the points of the point clouds. The model manager 202 may be configured to down-sample the points of the point clouds in particular regions or portions of the digital models. For instance, the model manager 202 may be configured to down-sample the points of the point cloud in some portions of the digital model (e.g., the gingiva portion of the digital model corresponding to gingiva on the user's dental arch), and maintain points of the point cloud in other portions of the digital model (e.g., the teeth portion of the digital model corresponding to teeth on the user's dental arch). The model manager 202 may down-sample the points of the point cloud temporarily (e.g., for purposes of alignment) while adding those down-sampled points back into the digital model or into the merged model or aligned models, or remove at least some of the points of the point cloud (e.g., to decrease computing requirements, and increase computing performance and the speed at which models can be merged). In some embodiments, the model manager 202 can down-sample or eliminate unnecessary points from a digital model or the merged model based on the unnecessary points being located on a part of the model that is irrelevant or less importance than other parts of the model to manufacturing aligners. For example, the model manager 202 can down-sample or eliminate points located a threshold distance from a gingival-tooth interface of the model (e.g., greater than 3 mm, greater than 5 mm, greater than 1 cm). By down-sampling or eliminating points that are irrelevant or less important than other parts of the model to manufacturing aligners, the model manager 202 can more quickly perform merges and other functions with respect to the models.

At step 1125, the computing device 100 computes point normals. In some implementations, the model manager 202 generates the point normals for each of the generated points for the point clouds (e.g., generated at step 1120). Together, the generated points (e.g., at step 1120) and point normals (e.g., computed at step 1125) represent, form, or otherwise define the point cloud. As stated above, each point normal includes a vector extending outwardly from the points of the point cloud. The vector may extend outwardly from the points of the point cloud orthogonally from the surface of the digital model. Each point of the point cloud may include a corresponding point normal.

In some implementations, the point normals are surface normals. The surface normals may be or include a vector which extends orthogonally from a geometric face corresponding to a point of the point cloud. Each point may correspond to a vertex for a geometric face. The geometric face extends along a plane. The model manager 202 is configured to compute the surface normal for the plane along which the geometric face extends. The model manager 202 is configured to apply, use, or define the point normal for the points corresponding to the vertices of a given geometric face as the computed normal for the plane corresponding to the geometric face.

In some implementations, the point normals are vertex normals. The vertex normals may be or include a vector which extends perpendicular to two vectors. The two vectors may be two adjacent edges of the geometric face (e.g., which connect to form a vertex). In other words, a vertex normal for a vertex of a geometric face is defined as a vector extending perpendicular to the two edges which form the vertex of the geometric face. The model manager 202 is configured to compute the vertex normal for each of the points. The model manager 202 may compute the vertex normal by identifying the edges of each geometric face which form the vertex. The model manager 202 may compute the vertex normal by computing a cross-product of the edges which form the vertex.

At step 1130, the computing device 100 computes a translation matrix. In some implementations, the model manager 202 computes the translation matrix using the first point cloud and the second point cloud (e.g., generated at step 1110). The translation matrix may be a matrix comprising a shift of each of the points of one of the point clouds to align the first point cloud and second point cloud. The translation matrix may be a shift of the first point cloud relative to the second point cloud (or vice versa). In some implementations, the translation matrix may be computed using algorithms which implement a combination of rough (or global) alignment and fine (or local) alignment. As one example, the model manager 202 may compute the translation matrix using RANdom Sample Consensus (RANSAC) for global alignment of the first and second point cloud, and Iterative Closest Point (ICP) for local alignment. In some implementations, the model manager 202 first computes the translation matrix using RANSAC then refines, modifies, or otherwise adjusts the translation matrix using ICP.

At step 1135, the computing device 100 shifts the first or the second point cloud based on the translation matrix (e.g., computed at step 1130). In some implementations, the model manager 202 shifts the points of the first or second point cloud by the shifts specified in the translation matrix to align the first and second point cloud. Each point may be shifted according to the translation matrix. The model manager 202 shifts the points of the first or second point cloud to minimize the distance between two corresponding points of the point clouds. In some implementations, the model manager 202 may iteratively perform steps 1130 and 1135 (e.g., computation of the translation matrix and shifting the first or second point cloud). The model manager 202 may iteratively perform steps 1130 and 1135 to minimize the distance between the points so as to more closely align the first and second point clouds. As the first point cloud and second point cloud are generated based on separate digital models, the first and second point clouds may not necessarily be perfectly aligned. However, the model manager 202 may iteratively perform steps 1130 and 1135 so as to align the first and second model without regard to differences between the first and second model (e.g., to best align the first and second model).

The model manager 202 may iteratively perform steps 1130 and 1135 to best align the first and second point cloud. The model manager 202 may perform steps 1130 and 1135 a predetermined number iterations. The predetermined number may be selected automatically based on an average number of iterations for the point clouds being sufficiently aligned according to one or more metrics, such as a Root Mean Square (RMS) error. For instance, the predetermined number may be 1 iteration, 2 iterations, 5 iterations, 10 iterations, 20 iterations, 100 iterations, etc. The predetermined number may be selected by a user, such as an operator or IT manager of the computing device 100 based on a balance between computing requirements and accuracy. In some implementations, the model manager 202 performs steps 1130 and 1135 until the RMS error for corresponding points of the point cloud satisfies a threshold (e.g., an RMS error of 0.5 mm, 0.55 mm, 0.6 mm, 0.65 mm, 0.7 mm, 0.75 mm, 0.8 mm, 0.85 mm, 0.9 mm, 0.95 mm, etc.). The model manager 202 may shift the points of the point cloud(s), and compute an RMS error for corresponding points of the point clouds. The model manager 202 may compute the RMS error for each of the points, a subset of the points, etc.

Once the model manager 202 aligns the first and second point cloud, the computing device 100 generates a merged model (e.g., a model which includes at least some portions of the first and second point cloud). In some implementations, prior to generating the merged model, the computing device 100 may convert the aligned point clouds into STL files. The computing device 100 may use the aligned point clouds or aligned STL files for generating the merged model. The computing device may generate the merged model as described in greater detail above (e.g., starting at step 408 of FIG. 4, for instance).

Through automating alignment of the models, the systems and methods described herein provide numerous advantages and improvements over other systems and methods for merging models. For example, by generating point clouds and automatically aligning those point clouds to generate a merged model, the aligned point clouds, and thus the models, are more accurately aligned than could otherwise be achieved if relying on user inputs, which require a user to manually select common points on the models to be merged. Manually selecting common points on different models for alignment is not as accurate the automatic alignment of point clouds disclosed herein, as manual inputs are prone to human error and other inaccuracies. Automated alignment of the point clouds, and thus the models, also eliminates delays caused by waiting for manual inputs, which improves upon prior systems and method by increasing the speed at which models can be merged, thereby also decreasing the overall time needed to prepare dental models for manufacturing dental aligners. Through improving the accuracy of the alignment of the models, the merged model generated by the systems and methods described herein are a more accurate representation of a user's dentition as compared to merged models that rely on a user selection of common points of the models to be merged. Using a more accurate merged model to manufacture dental aligners results in creating dental aligners that better fit a user's dentition, thereby resulting in dental aligners that are more comfortable to wear and that result in more accurate treatment outcomes. By increasing the accuracy of treatment outcomes, the need to retreat a user is reduced or eliminated.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.). By way of example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on memory or other machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products or memory comprising machine-readable media for carrying or having machine-executable instructions or data structures stored thereon. Such machine-readable media may be any available media that may be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, by way of example, instructions and data which cause a general purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision step.

What is claimed is:

1. A computing device for dental impression scan merging, the computing device comprising:
a processor configured to:
generate a first model and a second model, the first model comprising a first three-dimensional model including a first plurality of geometric faces indicative of a first dental impression of a dental arch of a user, the second model comprising a second three-dimensional model including a second plurality of geometric faces indicative of a second dental impression of the same dental arch of the user, the first model and the second model having a common anatomical feature;
generate a first point cloud of the first model and a second point cloud of the second model;
align the first point cloud and the second point cloud using the common anatomical feature of the first model and the second model, wherein aligning the first point cloud and the second point cloud comprises:
down-sampling points from the first point cloud and from the second point cloud in a gingiva portion of the first model and the second model that is located at least a threshold distance from a gingival-tooth interface; and
aligning the down-sampled first point cloud and the down-sampled second point cloud; and
merge the first model and the second model to generate a merged model, wherein merging the first model and the second model is based on the alignment of the first point cloud and the second point cloud.

2. The computing device of claim 1, wherein the processor is further configured to transmit information associated with the merged model or to use the information associated with the merged model to manufacture a dental aligner specific to the dental arch of the user and being configured to reposition one or more teeth of the user.

3. The computing device of claim 1, wherein generating the first point cloud and the second point cloud comprises, for each of the first model and the second model:
identifying vertices of the plurality of geometric faces;
generating, the vertices of the plurality of geometric faces, points for a point cloud; and
computing, for the generated points of the point cloud, a point normal.

4. The computing device of claim 3, wherein aligning the first point cloud and the second point cloud comprises:
computing, using the first point cloud and the second point cloud, a translation matrix; and
shifting the first point cloud with respect to the second point cloud based on the computed translation matrix to align the first point cloud and the second point cloud.

5. The computing device of claim 3, wherein the computed normals are surface normals that extend orthogonally from the surface of the model.

6. The computing device of claim 3, wherein each point corresponds to a vertex of one of the plurality of geometric faces, and wherein the computed normals are vertex normals which extend from the vertices, the vertex normals being computed using a cross product of two edges which form a corresponding vertex.

7. The computing device of claim 1, wherein the processor is configured to compute a Root Mean Square (RMS) value between a first point of the first point cloud and a second point of the second point cloud, wherein the first point corresponds with the second point.

8. The computing device of claim 7, wherein the processor is configured to iteratively compute a plurality of translation matrices for shifting one of the first point cloud or the second point cloud to align the first point cloud and the second point cloud based on the computed translation matrices until the RMS value satisfies a threshold.

9. The computing device of claim 1, wherein the processor is configured to iteratively compute a plurality of translation matrices for shifting one of the first point cloud or the second point cloud to align the first point cloud and the second point cloud based on the computed translation matrices a predetermined number of iterations.

10. A method comprising:
generating, by a computing device, a first model and a second model, the first model comprising a first three-dimensional model including a first plurality of geometric faces indicative of a first dental impression of a dental arch of a user, the second model comprising a second three-dimensional model including a second plurality of geometric faces indicative of a second dental impression of the same dental arch of the user, the first model and the second model having the common anatomical feature;

generating, by the computing device, a first point cloud of the first model and a second point cloud of the second model;

aligning, by the computing device, the first point cloud and the second point cloud using the common anatomical feature of the first model and the second model, wherein aligning the first point cloud and the second point cloud comprises:

down-sampling points from the first point cloud and from the second point cloud in a gingiva portion of the first model and the second model that is located at least a threshold distance from a gingival-tooth interface; and aligning the down-sampled first point cloud and the down-sampled second point cloud; and merging, by the computing device, the first model and the second model to generate a merged model, wherein merging the first model and the second model is based on the alignment of the first point cloud and the second point cloud;

wherein generating the first point cloud and the second point cloud comprises, for each of the first model and the second model:

identifying, by the computing device, vertices of the plurality of geometric faces;

generating, by the computing device using the vertices of the plurality of geometric faces, points for a point cloud; and computing, by the computing device for the generated points of the point cloud, a point normal.

11. The method of claim 10, wherein aligning the first point cloud and the second point cloud comprises:

computing, by the computing device using the first point cloud and the second point cloud, a translation matrix; and shifting, by the computing device, the first point cloud with respect to the second point cloud based on the computed translation matrix to align the first point cloud and the second point cloud.

12. The method of claim 10, wherein the computed normals are surface normals that extend orthogonally from the surface of the model.

13. The method of claim 10, wherein each point of the point clouds correspond to a vertex of one of the plurality of geometric faces, and wherein the computed normal are vertex normals extending from a vertex of one of the plurality of geometric faces, the vertex normals being computed using a cross product of two edges which form a corresponding vertex.

14. The method of claim 10, further comprising computing, by the computing device, a Root Mean Square (RMS) value between a first point of the first point cloud and a second point of the second point cloud, wherein the first point corresponds with the second point.

15. The method of claim 14, wherein the steps of computing the translation matrix and shifting one of the first point cloud or the second point cloud are iteratively performed until the RMS value satisfies a threshold.

16. The method of claim 10, further comprising manufacturing, based on the merged model, a dental aligner specific to the dental arch of the user and being configured to reposition one or more teeth of the user.

17. A computing device for dental impression scan merging, the computing device comprising:

a processing circuit including a processor and memory, the memory storing instructions that are configured to be executed by the processor to cause the processor to:

generate a first model and a second model, the first model comprising a first three-dimensional model including a first plurality of geometric faces indicative of a first dental impression of a dental arch of a user, the second model comprising a second three-dimensional model including a second plurality of geometric faces indicative of a second dental impression of the same dental arch of the user, the first model and the second model having the common anatomical feature;

generate a first point cloud for the first model and a second point cloud for the second model, wherein generating the first point cloud and the second point cloud comprises, for each of the first model and the second model:

identifying vertices of the plurality of geometric faces;

generating, using the vertices of the plurality of geometric faces, points that together define a point cloud for the respective model;

compute, using the first point cloud and the second point cloud, a translation matrix;

shift the first point cloud with respect to the second point cloud based on the translation matrix to align the first point cloud and the second point cloud using the common anatomical feature of the first model and the second model, wherein shifting the first point cloud with respect to the second point cloud comprises:

down-sampling points from the first point cloud and from the second point cloud in a gingiva portion of the first model and the second model that is located at least a threshold distance from a gingival-tooth interface; and shifting the down-sampled first point cloud and the down-sampled second point cloud based on the translation matrix; and generate a merged model that includes data from the first model and the second model based on the alignment of the first point cloud and the second point cloud.

18. The computing device of claim 17, wherein the memory further stores instructions that are configured to be executed by the processor to cause the processor to manufacture a dental aligner based on the merged model, the dental aligner being specific to the dental arch of the user and being configured to reposition one or more teeth of the user.

19. The computing device of claim 17, wherein the memory further stores instructions that are configured to be executed by the processor to cause the processor to compute a Root Mean Square (RMS) value between two corresponding points of the first point cloud and the second point cloud; and wherein the instructions cause the processor to iteratively compute translation matrices and shift one of the first point cloud or the second point cloud based on the computed translation matrices until the RMS value satisfies a threshold.

20. The computing device of claim 17, wherein the instructions cause the processor to iteratively compute translation matrices and shift one of the first point cloud or the second point cloud based on the computed translation matrices a predetermined number of iterations.

* * * * *